(12) United States Patent
Zeng

(10) Patent No.: US 10,034,866 B2
(45) Date of Patent: *Jul. 31, 2018

US010034866B2

(54) INHALABLE MEDICAMENT COMPRISING TIOTROPIUM

(71) Applicant: TEVA Branded Pharmaceutical Products R&D, Inc., Horsham, PA (US)

(72) Inventor: Xian-Ming Zeng, Miami, FL (US)

(73) Assignee: TEVA Branded Pharmaceutical Products R&D, Inc., Horsham, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/285,584

(22) Filed: Oct. 5, 2016

(65) Prior Publication Data

US 2017/0020852 A1    Jan. 26, 2017

Related U.S. Application Data

(63) Continuation of application No. 14/367,031, filed on Jun. 19, 2014, now Pat. No. 9,655,969.

(51) Int. Cl.
| | |
|---|---|
| *A61K 31/519* | (2006.01) |
| *A61K 31/58* | (2006.01) |
| *A61K 9/12* | (2006.01) |
| *A61K 31/439* | (2006.01) |
| *A61K 47/10* | (2017.01) |
| *A61K 47/12* | (2006.01) |
| *A61K 9/00* | (2006.01) |
| *A61M 11/02* | (2006.01) |
| *A61M 15/00* | (2006.01) |

(52) U.S. Cl.
CPC ............ *A61K 31/439* (2013.01); *A61K 9/008* (2013.01); *A61K 47/10* (2013.01); *A61K 47/12* (2013.01); *A61M 11/02* (2013.01); *A61M 15/009* (2013.01)

(58) Field of Classification Search
CPC .... A61K 9/008; A61K 9/0073; A61K 9/0078; A61K 9/0075
See application file for complete search history.

(56) References Cited

U.S. PATENT DOCUMENTS

| | | | |
|---|---|---|---|
| 5,447,150 A | 9/1995 | Bacon et al. | |
| 5,610,163 A | 3/1997 | Banholzer et al. | |
| 5,676,930 A * | 10/1997 | Jager | A61K 9/008 424/45 |
| 6,258,341 B1 | 7/2001 | Foster | |
| 6,589,560 B2 | 7/2003 | Foster et al. | |
| 6,654,466 B1 | 11/2003 | Keller et al. | |
| 7,347,199 B1 * | 3/2008 | Lewis | A61K 9/008 128/200.23 |
| 2002/0025299 A1 | 2/2002 | Lewis | |
| 2002/0169321 A1 | 11/2002 | Banholzer et al. | |
| 2003/0070679 A1 | 4/2003 | Hochrainer et al. | |
| 2003/0087927 A1 | 5/2003 | Sieger et al. | |
| 2003/0171586 A1 | 9/2003 | Banholzer et al. | |
| 2004/0002510 A1 | 1/2004 | Bender et al. | |
| 2004/0018153 A1 | 1/2004 | Schmelzer | |
| 2004/0126325 A1 | 7/2004 | Lewis | |
| 2005/0058606 A1 * | 3/2005 | Six | A61K 9/008 424/46 |
| 2005/0121027 A1 | 6/2005 | Nilsson et al. | |
| 2005/0143410 A1 | 6/2005 | Pfrengle et al. | |
| 2005/0201951 A1 | 9/2005 | Barr et al. | |
| 2006/0079544 A1 | 4/2006 | Viel et al. | |
| 2006/0193785 A1 * | 8/2006 | Lewis | A61K 9/008 424/45 |
| 2006/0246009 A1 | 11/2006 | Morissette et al. | |
| 2007/0088030 A1 | 4/2007 | Niklaus-Humke et al. | |
| 2007/0092453 A1 | 4/2007 | Pop et al. | |
| 2007/0128123 A1 | 6/2007 | Six et al. | |
| 2007/0189979 A1 | 8/2007 | Zeng et al. | |
| 2007/0225314 A1 | 9/2007 | Diulgheroff et al. | |
| 2009/0088408 A1 | 4/2009 | Meade et al. | |
| 2009/0163531 A1 | 6/2009 | Engel et al. | |
| 2010/0009984 A1 | 1/2010 | Samburski et al. | |
| 2010/0326437 A1 | 12/2010 | Zeng | |
| 2012/0085345 A1 | 4/2012 | Zeng | |
| 2013/0302260 A1 | 11/2013 | Berner et al. | |

FOREIGN PATENT DOCUMENTS

| | | | |
|---|---|---|---|
| CA | 2395653 | 4/2002 | |
| CN | 1328445 | 12/2001 | |
| EP | 0372777 | 6/1990 | |
| EP | 0418716 | 3/1991 | |
| EP | 0616525 | 9/1994 | |
| EP | 1238661 | 9/2002 | |
| EP | 1401445 | 3/2004 | |
| EP | 1468998 | 10/2004 | |
| EP | 1487832 | 12/2004 | |
| EP | 1508330 | 2/2005 | |
| EP | 166029 | 6/2006 | |
| EP | 1682542 | 7/2006 | |
| EP | 1923393 | 5/2008 | |
| EP | 2201934 | 6/2010 | |
| EP | 2201934 A1 * | 6/2010 | ............. A61K 9/008 |

(Continued)

OTHER PUBLICATIONS

U.S. Appl. No. 12/668,546, filed Apr. 15, 2010, Zeng.
U.S. Appl. No. 14/151,172, filed Jan. 9, 2014, Norton Healthcare Ltd.
U.S. Appl. No. 14/367,036, filed Jun. 19, 2014, TEVA Branded Pharmaceutical Products R&D, Inc.

(Continued)

*Primary Examiner* — Tracy Liu
(74) *Attorney, Agent, or Firm* — Baker & Hostetler LLP

(57) ABSTRACT

This invention relates to a solution formulation comprising a tiotropium salt, 12-20% ethanol, 0.1-1.5% of water, 0.05-0.10% citric acid (or other organic acid) and an HFA propellant, wherein the percentages are percentages by weight based on the total weight of the formulation. The invention also provides a p MDI comprising a canister containing the formulation.

6 Claims, No Drawings

(56) References Cited

FOREIGN PATENT DOCUMENTS

| | | |
|---|---|---|
| EP | 2201943 | 6/2010 |
| GB | 2264238 | 8/1993 |
| JP | 2009-234333 | 9/2009 |
| WO | WO 1992/09323 | 6/1992 |
| WO | WO 1993/11743 | 6/1993 |
| WO | WO 1994/13262 | 6/1994 |
| WO | WO 1998/05302 | 2/1998 |
| WO | WO 2000/28979 | 5/2000 |
| WO | WO 00/30608 | 6/2000 |
| WO | WO 2000/030608 | 6/2000 |
| WO | WO 2001/93933 | 12/2001 |
| WO | WO 2002/30928 | 4/2002 |
| WO | WO 2003/082252 | 10/2003 |
| WO | WO 2004/017942 | 3/2004 |
| WO | WO 2004/054580 | 7/2004 |
| WO | WO 2005/020953 | 3/2005 |
| WO | WO 2005/027875 | 3/2005 |
| WO | WO 2011/058606 | 3/2005 |
| WO | WO 2006/134021 | 12/2006 |
| WO | WO 2007/075858 | 7/2007 |
| WO | WO 2007/121913 | 3/2008 |
| WO | WO 2013/092237 | 6/2013 |
| WO | WO 2013/092345 | 6/2013 |
| WO | WO 2013/127738 | 9/2013 |

OTHER PUBLICATIONS

U.S. Appl. No. 14/620,929, filed Feb. 12, 2015, Norton Healthcare Ltd.

U.S. Appl. No. 15/285,584, filed Oct. 5, 2016, TEVA Branded Pharmaceutical Products R&D, Inc.

Boehringer Ingelheim, Spiriva Respimat, 2.5 Microgram, Solution for Inhalation, Package Leaflet, approved Aug. 2010.

Brusasco et al, Tiotropium Reduced Exacerbations and Health Resource use in COPD; Thorax 58, pp. 399-404, 2003.

English translation of Korean Office Action for Application No. 10-2014-7017716, dated Nov. 2, 2015.

Ethanol-Wasser-Dichtetabelle—Internet Chemie-Lexikon; Opposition against EP-B-2 606 891; Oct. 19, 2016.

European Notice of Opposition dated Aug. 10, 2015 in European Application No. 12196725.1.

European Notice of Opposition dated Aug. 18, 2015 in European Application No. 12196725.1.

ICH Harmonised Tripartite Guideline; Stability Testing of New Drug Substances and products; Opposition against EP-B-2 606 891; Feb. 6, 2003.

J.P. Mitchell and M.W. Nagel "Particle Size Analysis of Aerosols from Medicinal Inhalers" Kona No. 22 (2004) 32-65.

Malcolmson R.J. et al., "Dry Powder Formulation for Pulmonary Delivery" Pharmaceuticals Science and Technology Today, Elsevier Trends Journals, Cambidge, GB, vol. 1, No. 9, Dec. 1, 1998, pp. 394-398.

Petition filed by the patentee on May 3, 2013 and official communication issued by the EPO on Jun. 21, 2013 for European Application No. 12196725.1.

Rennard, "Treatment of Stable Chronic Obstructive Pulmonary Disease", Lancet, 364, pp. 791-802, 2004.

S.L. Spector (editor), Anticholinergic Agents in the Upper and Lower Airways, Marcel Dekker, Inc., pp. 35-38 (1999; e-Library ed. 2005).

Search Report for International Application No. PCT/EP2012/074690, dated Mar. 26, 2013, dated Apr. 3, 2013.

Search Report for International Application No. PCT/EP2012/075230, dated Mar. 8, 2013, dated Mar. 19, 2013.

Spiriva Respimat 2.5 Microgram, solution for inhalation, Public Assessment Report of the Medicines Evaluation Board in the Netherlands, 26 pages, Date of first publication: Feb. 1, 2008; Last revision: Apr. 19, 2011.

Van Noord, "A Randomised Controlled Comparison of Tiotropium and Ipratropium in the Treatment of Chronic Obstructive Pulmonary Disease", Thorax 55:289-294 (2000).

Vervaet and Byron, "Drug-Surfactant-propellant interactions in HFA-Formulations", International Journal of Pharmaceutics, 186, pp. 13-30, 1999.

\* cited by examiner

INHALABLE MEDICAMENT COMPRISING TIOTROPIUM

CROSS-REFERENCE TO RELATED APPLICATIONS

This application is a continuation of U.S. application Ser. No. 14/367,031, filed Jun. 19, 2014, which is the National Stage Entry of International Application No. PCT/EP2012/074690, filed Dec. 6, 2012, which claims the benefit of U.S. Provisional Application No. 61/577,315, filed Dec. 19, 2011 and Great Britain Application No. 1200525.2, filed Jan. 13, 2012, the entireties of which are incorporated herein by reference.

FIELD OF THE INVENTION

The present invention relates to an inhalable medicament and more specifically to a solution formulation of tiotropium.

BACKGROUND OF THE INVENTION

Tiotropium is an anticholinergic agent and is indicated as a maintenance bronchodilator treatment to relieve symptoms of patients with chronic obstructive pulmonary disease (COPD). Tiotropium is marketed as Spiriva® in the form of an inhalation powder or solution for inhalation.

The present invention is directed to a formulation of tiotropium. Tiotropium contains a quaternary ammonium cation and is typically used as the bromide salt which has the following structure:

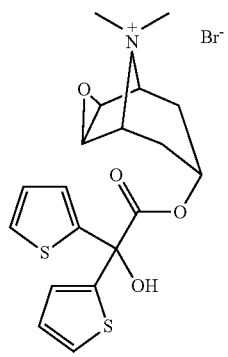 [SMILES: C[N+]1(C)C2CC(OC(=O)C(O)(c3cccs3)c3cccs3)CC1C1OC12 ; [Br-]]

The two most common approaches for formulating inhalable medicaments for use outside of the emergency room are the dry powder inhaler (DPI) and the pressurised metered dose inhaler (pMDI). An example of the DPI is the marketed inhalation powder. The inhalation powder contains tiotropium bromide monohydrate and lactose stored in a hard capsule and is administered using the HandiHaler® dry powder inhaler. However, the pMDI is an alternative approach to delivering tiotropium bromide to the lungs. Typically patient compliance is greater with a pMDI as they tend to be easier to use. Moreover, the DPI suffers from the drawback that only a small portion of the powdered active ingredient is actually inhaled into the lungs.

pMDI formulations may be presented as suspensions or solutions. WO 03/082252 provides an example of tiotropium bromide monohydrate in HFA 134a or 227 formulated as a suspension. In a solution formulation, the active ingredient is dissolved in the propellant system and hence avoids problems such as potential blockage of the pMDI dispensing nozzle orifice, physical instability of the suspended particles and the requirement to use suspending agents such as surfactants. Solution formulations are also easier to manufacture. However, a significant problem associated with formulating tiotropium salts as a solution formulation is that the active ingredient is chemically unstable in the presence of the co-solvents, such as ethanol, required to solubilise the active ingredient in the HFA propellant.

The marketed solution for inhalation circumvents this problem by avoiding the pMDI altogether. Instead, the product employs the Respimat® "soft-mist inhaler". The formulation contains tiotropium bromide, benzalkonium chloride, disodium edetate, purified water and hydrochloric acid 3.6% (for pH adjustment). Instead of using a liquefied propellant, the Respimat® inhaler produces a mist by the action of a spring within the inhaler. However, the pMDI is a preferred approach and a number of attempts have been made to formulate tiotropium as a pMDI formulation.

WO 94/13262 discloses the use of inorganic or organic acids to stabilise solution formulations. However, the disclosure therein is principally directed to ipratropium bromide and it is not apparent how the approach should be modified to apply to tiotropium.

US 2005/0058606 addresses the problem of stabilising a tiotropium bromide solution formulation also using inorganic or organic acids.

However, significant concerns have arisen over the use of acids to stabilise solution formulations as the acids themselves can react with the metallic surface of the canister leading to the leaching of metal salts into the formulation which can lead to further instability of the active ingredient and/or contamination of the formulation. For example, EP 1 666 029 discloses pMDI solution formulations in which the internal surfaces of the inhaler consist of stainless steel or anodised aluminium, or in which the internal surfaces are lined with an inert organic coating, in order to minimise the effects of the canister on the chemical instability of the active ingredient. In addition, EP 2 201 934 describes a pMDI formulation containing a tiotropium salt, an HFA propellant, one or more co-solvents and a mineral acid. This document teaches the importance of using an aerosol can fitted with sealing rings and gaskets which are in contact with the formulation, made of a butyl or halo-butyl rubber, in order to avoid adverse interactions of the acid-containing formulation with the materials of the rings and gaskets.

There remains, therefore, a need in the art for pMDI solution formulations of tiotropium salts which are chemically stable and which do not adversely react with the internal surfaces of the inhaler.

SUMMARY OF THE INVENTION

Accordingly, the present invention provides a solution formulation comprising a tiotropium salt, 12-20% ethanol, 0.1-1.5% of water, 0.05-0.10% citric acid and an HFA propellant, wherein the percentages are percentages by weight based on the total weight of the formulation.

This formulation provides a precise limitation in the absolute and relative amounts of the ethanol, water and citric acid in order to provide a high degree of chemical stability to the active ingredient without adversely affecting the material of the inhaler.

The formulation of the present invention is a solution formulation and hence the formulation is a single homogeneous phase. The tiotropium salt and the citric acid are thus dissolved in the propellant/ethanol/water phase. The formulation can be cooled to 4° C. and then re-heated to ambient temperature without precipitation of the active ingredient.

As the formulation is a solution, the formulation does not require the presence of surfactants (which are used to stabilise suspended particles of the active ingredient in a suspension formulation). Accordingly, it is not necessary to add surfactant to the formulation and hence the formulation of the present invention is preferably substantially free of surfactant (e.g. the formulation contains less than 0.0001% by weight of surfactant based on the total weight of the formulation).

DETAILED DESCRIPTION OF THE INVENTION

The formulation contains the tiotropium salt, 12-20% ethanol, 0.1-1.5% of water, 0.05-0.10% citric acid and an HFA propellant. All of the percentages are percentages by weight based on the total weight of the formulation, i.e. the total weight of the active ingredient and all excipients present. Preferably, the formulation contains 0.15 to 0.75% water.

The present invention is applicable to tiotropium salts generally, but preferably the present formulation contains tiotropium bromide which is the most commonly used salt and the salt presently on the market. The preferred quantities of excipients set out herein are particularly, but not exclusively, designed for use with tiotropium bromide as the tiotropium salt.

The amount of tiotropium salt present will vary depending on the dose of tiotropium which is required for the particular product. Typically, the tiotropium salt (preferably the bromide) is present in an amount to provide 1-10 micrograms of tiotropium base, ex valve, per actuation. Preferably, 2-6 micrograms of tiotropium base, ex valve, per actuation. That is, the amount of free base equivalent in the metered dose as measured as it leaves the valve. This corresponds to a preferred amount of tiotropium bromide of 0.00422-0.02110 wt %.

The ethanol is preferably dehydrated ethanol according to the USP. The ethanol is principally present to solubilise the tiotropium salt. In a preferred embodiment, the amount of ethanol is 12-15%. The water is preferably purified water, according to the USP. The water is preferably present at 0.30-0.60%. The citric acid is preferably anhydrous citric acid according to the USP. In another preferred embodiment, the amount of citric acid is 0.05-0.08%. It is believed that the relatively high concentration of citric acid provides the required chemical stability to the tiotropium salt. However, retaining a relatively low level of water prevents the citric acid from degrading the canister.

It is particularly preferred that the amounts are simultaneously 12-15% ethanol, 0.30-0.60% water and 0.05-0.08% citric acid. More preferably, the components are present at about 15% ethanol, about 0.5% of water and about 0.06% citric acid.

The formulation also contains a hydrofluoroalkane (HFA) propellant. Such propellants are well known in the art. The preferred HFAs of the present invention are HFA 134a and/or HFA 227. Preferably HFA 134a is used.

On actuation of the inhaler, a metered dose of the formulation is released from the inhaler. The metered dose of the formulation passes through the valve stem and stem block where it is discharged via an orifice in the dispensing nozzle of the stem block into the mouthpiece and hence to the patient. On release, the propellant rapidly evaporates leaving the active ingredient dissolved in small droplets of ethanol and water which will in turn evaporate to some extent. The particle size of the droplets will depend on a number of factors, including the precise amounts of ethanol and water used, the size of the orifice in the dispensing nozzle, the spray force, the plume geometry, etc. Typically, however, the droplets will be less than 5 microns in diameter. For some applications, the droplet sizes will be too small for optimal lung deposition. In such cases, glycerol may be added to the formulation. Glycerol is less volatile than ethanol and hence experiences less evaporation on actuation, thereby providing larger droplets (by larger is meant that they have a higher mass median aerodynamic diameter as measured by an NGI). Accordingly, in a preferred embodiment, the formulation of the present invention further comprises glycerol. In a particularly preferred embodiment, the formulation of the present invention consists of a tiotropium salt (preferably the bromide), 12-20% ethanol, 0.1-1.5% of water, 0.05-0.10% citric acid, an HFA propellant and optionally glycerol, in a preferred amount of 0.5-5%. The preferred amounts of the excipients set out hereinabove apply equally to this embodiment.

The solution formulation of the present invention is intended to be administered using a pressurised metered dose inhaler (pMDI). pMDIs are well known in the art; see, for example, Drug Delivery to the Respiratory Tract, Eds. D. Ganderton and T. Jones, VCH Publishers, 1987, pages 87-88, or Pharmaceutics—The Science of Dosage Form Design, Second Edition, Ed. M. E. Aulton, Churchill Livingstone, 2002, page 476 et seq for details).

pMDIs typically have a medicament-containing canister and an actuator housing having a mouthpiece. The canister is usually formed from an aluminium cup having a crimped lid which carries a metering valve assembly. The metering valve assembly is provided with a protruding valve stem which is inserted as a push fit into a stem block in the actuator housing.

To actuate, the user applies a compressive force to the closed end of the canister. The internal components of the metering valve assembly are spring loaded so that, typically, a compressive force of 15 to 30 N is required to activate the device. In response to this compressive force, the canister moves axially with respect to the valve stem by an amount varying between about 2 and 4 mm. This degree of axial movement is sufficient to actuate the metering valve and cause a metered quantity of the formulation to be expelled through the valve stem. This is then released into the mouthpiece via an orifice in the dispensing nozzle of the stem block. A user inhaling through the mouthpiece of the device at this point will thus receive a dose of the active ingredient.

An inhalation-actuated inhaler (also known as breath-actuated inhaler) is particularly preferred in order to prevent inadvertent actuation into the eye(s) of the patient. Suitable inhalers are disclosed in WO 92/09323, GB 2 264 238 and WO 01/93933. The present invention most preferably employs the inhaler as described with reference to FIGS. 3-5 of WO 92/09323.

The present invention further provides a pressurised metered dose inhaler comprising a canister, wherein the canister contains the solution formulation as described herein. The canister is located in the actuator housing as discussed hereinabove. The canister preferably contains 100 actuations or fewer, preferably about 60 actuations (i.e. a one-month supply, based on two actuations per dose). This is a relatively low quantity and hence the head space in the canister tends to be greater than with conventional pMDIs which provides an increased tendency for the tiotropium salt to degrade chemically. However, even in this more challenging environment, the formulation of the present invention is able to provide the required level of chemical stability. For example, a 10 mL brim-full-capacity canister may have a fill volume of 2.5-6.3 mL and a corresponding headspace volume of 7.5-3.7 mL. The valve is preferably a 25-63 microliter valve, more preferably a 25 or 50 microliter valve.

It has surprisingly been found that the formulation of the present invention is not only capable of reducing or preventing chemical degradation of the active ingredient, but also does not significantly affect the material of the canister (see Examples 2 and 3 set out hereinbelow). This provides the significant advantage that an uncoated aluminium canister may be used, thereby reducing the costs of the pMDI without adversely affecting the formulation. Thus, according to a preferred embodiment of the present invention, the pMDI comprises a canister composed of aluminium in which the internal surfaces are uncoated. It is envisaged that similar stabilising properties may be achieved using similar formulations of tiotropium bromide using other organic acids, such as ascorbic acid.

Accordingly, in a further aspect, the present invention provides a solution formulation comprising a tiotropium salt, 12-20% ethanol, 0.1-1.5% of water, 0.05-0.10% of an organic acid, preferably ascorbic acid, and an HFA propellant, wherein the percentages are percentages by weight based on the total weight of the formulation.

Preferably, the formulation contains 0.15 to 0.75% water. Other preferred embodiments of this aspect are identified in the dependent claims.

The present invention will now be described with reference to the following examples which are not intended to be limiting.

EXAMPLES

Example 1 (Reference Example)

Tiotropium bromide solution formulations were prepared using HFA 134a and ethanol only with ethanol concentrations of 8-15%. One such formulation consists of 0.08% w/w tiotropium bromide, 12% w/w ethanol and 88% w/w HFA 134a. The solution was cooled to 4° C. and then re-heated to CRT without precipitation of the drug. A rapid chemical degradation of the tiotropium bromide was observed.

Example 2

Batches of solution formulations were prepared by combining tiotropium bromide, ethanol, water and citric acid and mixing the components until a solution was formed. All formulations contained 0.0071% w/w tiotropium bromide and HFA 134a to 100% w/w. The solution was charged into an aluminium canister which was then sealed with a 50 microliter valve and filled with HFA 134a. All but batch H used an aluminium canister coated with FEP. The amounts of the excipients are set out in the following table.

| | Formulation Target (% w/w) | | |
|---|---|---|---|
| Batch | Ethanol | Water | Citric acid |
| A | 12 | 0.25 | 0.06 |
| B | | | 0.0035 |
| I | | 0.5 | 0.06 |
| J | | | 0.0035 |
| C | 15 | 0.25 | 0.06 |
| D | | | 0.0035 |
| E | | 0.5 | 0.06 |
| F | | | 0.0035 |
| H | | | 0.06 |
| G | | | 0 |

After 3 months only batches A, I, C, E and H were subjected to continued testing. The results are shown the following table (in which CRT represents controlled room temperature, i.e. 25° C./60% relative humidity and ACC represents accelerated stability testing conditions, i.e. 40° C., 75% relative humidity).

| | Composition (%) Citric acid, water, ethanol | 1 month | | 3 months | | 6 months | |
|---|---|---|---|---|---|---|---|
| Batch | Can | CRT | ACC | CRT | ACC | CRT | ACC |
| A | 0.06, 0.25, 12 Coated[1] | 97.5% | 98.0% | 98.8% | 92.6% | 102.5% | 91.7% |
| I | 0.06, 0.5, 12 Coated[1] | 95.7% | 97.2% | 96.8% | 91.0% | 96.6% | 85.1% |
| C | 0.06, 0.25, 15 Coated[1] | 98.0% | 97.5% | 97.9% | 95.8% | 106.1% | 95.2% |
| E | 0.06, 0.5, 15 Coated[1] | 97.5% | 100.1% | 97.5% | 92.7% | 103.5% | 94.0% |
| H | 0.06, 0.5, 15 Uncoated | 99.3% | 101.7% | 101.0% | 97.4% | 104.6% | 96.5% |

[1]FEP coated can.

The results show an acceptably low level of chemical degradation after 6 months. Batches E and H also show essentially the same results indicating that the formulation of the present invention can be tolerated in uncoated canisters.

Example 3

Given the significant risk that acidic formulation might corrode the aluminium canister, the uncoated canisters from batch H were investigated further. Firstly, the aluminium content of the formulation after 3 months was determined. The concentration was recorded as 1.59 ppm which does not represent a toxicological hazard. Secondly, the canister were subjected to surface analysis by SEM. Strips of 25 mm×15 mm dimensions were cut from the canister and their surfaces were examined using JEOL 840 SEM. Images were taken at three different locations (top, middle and bottom end of strip) using two magnifications (100× and 250×) and compared to the results obtained with an unused canister. No damage to the canisters used with the tiotropium bromide formulation were observed.

Example 4

Three suitable commercial formulations are as follows:

| Ingredient | Concentration (% w/w) | Concentration (% w/w) | Concentration (% w/w) |
|---|---|---|---|
| Tiotropium bromide | 0.01107 | 0.01107 | 0.00716% |
| Ethanol, anhydrous, EP | 20.0 | 20.0 | 15.0% |
| Citric acid, EP | 0.06 | 0.06 | 0.06% |
| Purified water, EP | 0.50 | 0.50 | 0.50% |
| Glycerol EP | 1.50 | — | — |
| HFA 134a | 77.93 | 79.43 | 84.43% |
| Total | 100.0 | 100.0 | 100.0 |

They deliver 5.25 µg tiotropium as 6.3 µg tiotropium bromide (ex-valve) per actuation from a 50 µL metering valve.

A suitable mixing process for the concentrate sub-batch is as follows:

| Step | Description |
|---|---|
| 1 | Dispense the citric acid into a mixing container |
| 2 | Add the purified water to the mixing container and thoroughly dissolve the citric acid. Stir until dissolved and visually clear. |
| 3 | Add the ethanol to the container and continue to mix for about 5 minutes. |
| 4 | Add the tiotropium bromide to the mixing container, cap, and thoroughly mix until visibly dissolved. Then mix for additional 10 minutes. |

A suitable process for filling the concentrate sub-batch into pMDI canisters is as follows:

| Step | Description |
|---|---|
| 1 | Place empty canisters into vial racks capable of holding 60 canisters each. |
| 2 | Dispense target (approx. 3.51 mL) of the drug concentrate into aluminium pMDI canisters |
| 3 | Place a pMDI metering valve on each filled canister |
| 4 | Crimp the valve to the canister using a suitable pMDI valve crimper. |
| 5 | Add target amount of HFA 134a through the valve using pressure fill equipment. |
| 6 | Verify that the net fill weights are achieved using a balance or check weigher. |
| 7 | Print product and batch information on each canister. (e.g. product ID, lot number, date and serial number) |

Example 5

Assay and Related Substances

Assay and related substances are critical indicators of the chemical stability of the drug product and have been monitored for the first and third formulations in Example 4 under ACC and CRT storage conditions.

Assay data (% w/w) at initials and on stability for the third formulation in Example 4 were determined (average of n=3 units at each time-point). The formulations were tested in a valve upright orientation ("VU") and a valve down orientation ("VD"). The target concentration for this batch was 0.0071%. The results are set out in the following table:

| Condition | Time-point | VU | VD |
|---|---|---|---|
| Initial | 0 | 0.0071% | |
| CRT | 3 | 0.0070% | 0.0071% |
| | 6 | 0.0069% | 0.0068% |
| | 8 | 0.0071% | NA |
| | 9 | 0.0076% | 0.0073% |
| | 12 | 0.0065% | 0.0067% |
| | 18 | 0.0073% | 0.0072% |
| ACC | 3 | 0.0071% | 0.0068% |
| | 6 | 0.0068% | 0.0067% |
| INT | 1 | NA | 0.0068% |
| | 8 | NA | 0.0070% |

Five lots of the first formulation in Example 4 were also tested. The results are set out in the following table:

| | | Lot no. | | | | |
|---|---|---|---|---|---|---|
| Condition | Time Point (months) | I-120103 VD | I-120201 VU | I-120301 VD/VU | I-120401 VD/VU | I-120502 VD/VU |
| | Initial | 0.011% | 0.011% | 0.011% | 0.011% | 0.011% |
| CRT | 3 | 0.011% | 0.011% | N/A | N/A | N/A |
| | 6 | 0.011% | N/A | N/A | N/A | N/A |
| ACC | 1 | 0.011% | 0.011% | N/A | N/A | N/A |
| | 3 | 0.011% | 0.011% | N/A | N/A | N/A |
| | 6 | 0.011% | N/A | N/A | N/A | N/A |
| INT | 3 | 0.011% | N/A | N/A | N/A | N/A |

N/A: the stability time-points had not been reached when the data were compiled.

The assay data demonstrated that there was no change in the formulation concentration. Related substances data confirmed these findings.

Example 6

Delivered Dose Uniformity

Delivered dose uniformity was measured on the five batches of the first formulation from Example 4 at initials and on stability. The target delivered dose is 4.5 mcg/actuation of tiotropium, ex-actuator. Three canisters were measured for through-life DDU at each time-point for each stability condition. For each canister, ten ex-actuator doses were determined, three at the beginning (BOL), four at middle (MOL) and three at the end of canister life (EOL). The numerical averages for each time-point are summarised in the following table (average of n=30 at each time-point):

|  |  |  | Time Point (months) | | | |
|---|---|---|---|---|---|---|
| Lot | Condition | Orientation | 0 | 1 | 3 | 6 |
| I120103 |  | Initial | 4.9 | — | — | — |
|  | CRT | VD |  | — | 4.6 | 4.5 |
|  | ACC | VD |  | 4.8 | 4.8 | 4.6 |
| I120201 |  | Initial | 4.9 | — | — | — |
|  | CRT | VU |  | — | 4.8 | — |
|  | ACC | VU |  | 4.7 | 4.5 | — |
| I120301 |  | Initial | 4.7 | — | — | — |
| I120401 |  | Initial | 4.5 | — | — | — |
| I120502 |  | Initial | 4.3 | — | — | — |

The data demonstrate that the delivered dose is consistent through life-stage at all storage conditions and time-points tested with very little variability.

Example 7

Aerodynamic Particle Size Distribution

Aerodynamic particle size distribution (aPSD) was measured using the next generation impactor (NGI—apparatus E, Ph. Eur.) on the five batches of the first formulation from Example 4 at initials and on stability. These measurements were conducted at the beginning and end of canister life. The method used 20 actuations into the NGI per determination. The method used 20 actuations into the NGI per determination. The results were as follows (average of n=6 at each time-point):

|  | I-120103 VD | | I-120201 VU | | | | |
|---|---|---|---|---|---|---|---|
| Component | CRT 6 Months | ACC 6 Months | CRT 3 Months | ACC 3 Months | I-120301 Initial | I-120401 Initial | I-120502 Initial |
| Actuator (µg) | 0.4 | 0.5 | 0.3 | 0.4 | 0.4 | 0.3 | 0.3 |
| Adapter (µg) | 0.1 | 0.1 | 0.0 | 0.1 | 0.1 | 0.1 | 0.1 |
| Induction port (µg) | 2.4 | 2.3 | 2.8 | 2.6 | 2.6 | 2.6 | 2.4 |
| Stage 1 (µg) | 0.2 | 0.3 | 0.2 | 0.2 | 0.2 | 0.3 | 0.3 |
| Stage 2 (µg) | 0.1 | 0.2 | 0.1 | 0.1 | 0.1 | 0.1 | 0.1 |
| Stage 3 (µg) | 0.3 | 0.3 | 0.3 | 0.3 | 0.3 | 0.3 | 0.3 |
| Stage 4 (µg) | 0.6 | 0.5 | 0.5 | 0.5 | 0.6 | 0.6 | 0.6 |
| Stage 5 (µg) | 0.5 | 0.5 | 0.5 | 0.4 | 0.5 | 0.5 | 0.4 |
| Stage 6 (µg) | 0.2 | 0.2 | 0.2 | 0.2 | 0.2 | 0.2 | 0.2 |
| Stage 7 (µg) | 0.1 | 0.1 | 0.1 | 0.1 | 0.1 | 0.1 | 0.1 |
| MOC (µg) | 0.1 | 0.1 | 0.1 | 0.0 | 0.1 | 0.1 | 0.0 |
| FPD (µg) | 1.6 | 1.6 | 1.5 | 1.4 | 1.5 | 1.6 | 1.5 |
| FPF (%) | 35.6 | 34.3 | 32.4 | 31.5 | 32.7 | 33.8 | 33.8 |

The results show a consistent aPSD profile of tiotropium HFA BAI irrespective of the batches, their storage times and conditions. This is consistent with the performance of a solution formulation.

The invention claimed is:

1. A process for preparing a formulation in a canister comprising
   mixing citric acid, water, ethanol, and tiotropium bromide in a container to form a concentrate sub-batch;
   dispensing the concentrate sub-batch into a coated or uncoated aluminum canister; and
   adding an HFA propellant that is HFA 134a into the canister;
   wherein the formulation comprises 12-20% ethanol, 0.1-1.5% water, and 0.05-0.10% citric acid, wherein the percentages are by weight based on the total weight of the formulation.

2. The process according to claim 1, wherein the formulation further comprises glycerol.

3. The process according to claim 1, wherein the amount of ethanol is 12-15%, based on the total weight of the formulation.

4. The process according to claim 1, wherein the amount of water is 0.30-0.60%, based on the total weight of the formulation.

5. The process according to claim 1, wherein the amount of citric acid is 0.05-0.08%, based on the total weight of the formulation.

6. The process according to claim 1, wherein the weight ratio of tiotropium bromide to citric acid to water in the concentrate sub-batch is 1:5.4:45.2 or 1:8.4:69.8.

* * * * *